United States Patent
Heitger et al.

(10) Patent No.: US 7,608,722 B2
(45) Date of Patent: Oct. 27, 2009

(54) PREPARATION OF 1,7,'-DIMETHYL-2'-PROPYL-2,5'-BI-1H-BENZIMIDAZOLE

(75) Inventors: Helmut Heitger, Ingelheim (DE); Juan M. Rodriguez-Dehli, Mainz (DE); Rolf Dach, Gau-Algesheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 568 days.

(21) Appl. No.: 11/485,153

(22) Filed: Jul. 12, 2006

(65) Prior Publication Data

US 2007/0037986 A1  Feb. 15, 2007

(30) Foreign Application Priority Data

Jul. 22, 2005  (DE)  ........................ 10 2005 034 279

(51) Int. Cl.
*C07D 403/02*  (2006.01)
(52) U.S. Cl. ................................... 548/305.4
(58) Field of Classification Search ........................ None
See application file for complete search history.

(56) References Cited

OTHER PUBLICATIONS

Ries, Uwe, et al; 6-Substituted Benzimidazoles as New Nonpeptide Angiotensin II Receptor Antagonists: Synthesis, Biological Activity, and Structur-Activity Relationships; J. Med. Chem, 1993, 36, 4040-4051; XP-002135628.
Kaminski, Zbigniew; 2-Chloro-4,6-Disubstituted-1,3,5-Triazines, A Novel Group of Condensing Reagents, Tetrahedron Letters, vol. 26, No. 24, pp. 2901-2904, 1985, XP 001018670.
Venkataraman, K, and Wagle, D.R.; Cyanuric Chloride: A Useful Reagent for Converting Carboxylic Acids into Chlorides, Esters, Amides and Peptides; Tetrahedron Letters, vol. 32, pp. 3037-3040-XP 002403117.
Hipskind, Philip A., et al; Practical and Enantiospecific Synthesis of LY303870, a novel NK-1 Antagonist, J. Org. Chem. 1995, 60, 7033-7036; XP2403118A.

*Primary Examiner*—Kamal A Saeed
(74) *Attorney, Agent, or Firm*—Michael P. Morris; Mary Ellen M. Devlin; Timothy X. Witkowski

(57) ABSTRACT

A process for preparing 1,7'-dimethyl-2'-propyl-2,5'-bi-1H-benzimidazole of formula (I)

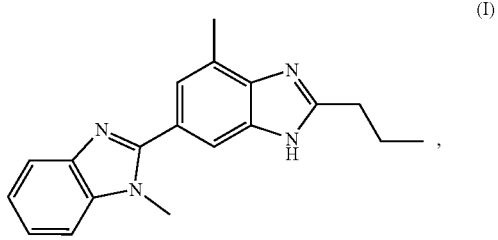

comprising:

reacting N-methyl-o-phenylenediamine of formula (II) or the salts thereof

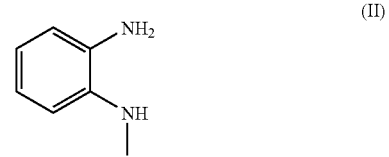

with 2-propyl-4-methyl-1H-benzimidazole-6-carboxylic acid of formula (III) or the salts thereof

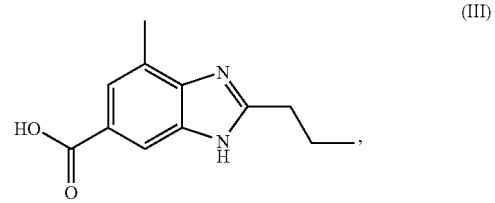

wherein the coupling and cyclization is achieved using 1,3,5-triazine and tertiary amine.

8 Claims, No Drawings

PREPARATION OF 1,7,'-DIMETHYL-2'-PROPYL-2,5'-BI-1H-BENZIMIDAZOLE

RELATED APPLICATIONS

This application claims priority to German Patent Application DE 10 2005 034 279.5, filed Jul. 22, 2005, which is hereby incorporated by reference in its entirety.

FIELD OF THE INVENTION

The invention relates to benzimidazoles substituted in the 2 position.

1,7'-Dimethyl-2'-propyl-2,5'-bi-1H-benzimidazole is used as an intermediate product in the large-scale synthesis of the pharmaceutically active substance telmisartan.

Ries et al., J. Med. Chem. (1993), 36(25), 4040-51, describe the preparation of 1,7'-dimethyl-2'-propyl-2,5'-bi-1H-benzimidazole by reacting 2-propyl-4-methyl-1H-benzimidazole-6-carboxylic acid with N-methyl-o-phenylenediamine in the presence of phosphoric acid.

WO 03/059890 describes the preparation of 1,7'-dimethyl-2'-propyl-2,5'-bi-1H-benzimidazole by reacting 2-propyl-4-methyl-1H-benzimidazole-6-carboxylic acid with N-methyl-o-phenylenediamine in the presence of methanesulfonic acid and phosphorus pentoxide.

In Tetrahedron Letters 26(24): 2901-2904 (1985) Kaminski describes 2-chloro-4,6-disubstituted-1,3,5-triazines which can be used as useful coupling reagents in peptide synthesis.

The present invention relates to an alternative process for preparing 1,7'-dimethyl-2'-propyl-2,5'-bi-1H-benzimidazole of formula (I)

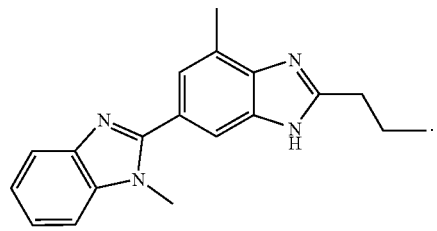

(I)

In this process N-methyl-o-phenylenediamine of formula (II) or the salts thereof

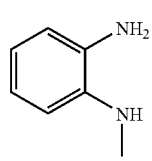

(II)

are coupled with 2-propyl-4-methyl-1H-benzimidazole-6-carboxylic acid of formula (III) or the salts thereof

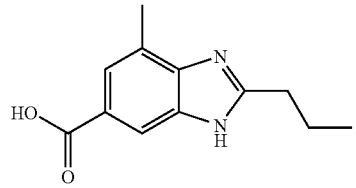

(III)

and cyclized in the presence of a 2-chloro-4,6-disubstituted-1,3,5-triazine and a tertiary amine, to form 1,7'-dimethyl-2'-propyl-2,5'-bi-1H-benzimidazole of formula (I).

As well as the compound of formula (II), it is also possible to use the salts thereof in this process. Preferred salts are the phosphate, perchlorate, chlorine, or bromine salt. The phosphate salt is particularly preferred. The latter can be described by the formula $$\text{[structure]} \cdot 0.77\, H_3PO_4.$$

Analogously, instead of 2-propyl-4-methyl-1H-benzimidazole-6-carboxylic acid of formula (III), it is also possible to use the salts thereof. Preferred salts are the salts with sodium or potassium. The free carboxylic acid is particularly preferred.

The coupling and cyclization of the two starting compounds are carried out in the presence of a 1,3,5-triazine. Examples of suitable triazines are 2,4,6-trichloro-1,3,5-triazine, 2-chloro-4,6-diphenoxy-1,3,5-triazine; 2-chloro-4,6-dibenzyloxy-1,3,5-triazine; 2-chloro-4,6-dimethoxy-1,3,5-triazine; 2,4-dichloro-6-phenoxy-1,3,5-triazine; 2,4-dichloro-6-benzyloxy-1,3,5-triazine; or 2,4-dichloro-6-methoxy-1,3,5-triazine. 2-Chloro-4,6-dialkoxy-1,3,5-triazines are preferred. 2-Chloro-4,6-dimethoxy-1,3,5-triazine is particularly preferred.

The triazine is activated beforehand with a tertiary amine. Examples of suitable tertiary amines are triethylamines, ethyldiisopropylamines, N-methylpyrrolidine, or N-methylmorpholine. Cyclic amines are preferred. N-Methylmorpholine is particularly preferred.

Suitable solvents for this process are polar solvents such as N,N-dimethylformamide, N,N-dimethylacetamide, dimethylsulfoxide, methanol, ethanol, and 2-propanol. Preferred solvents are methanol, ethanol and 2-propanol. Methanol is particularly preferred.

The first step of the reaction (activation of reagent) may be carried out in a temperature range from −10° C. to 25° C., preferably 0° C. to 15° C., and particularly preferably at 5° C. The second step of the reaction (amide formation) may be carried out in a temperature range of 0° C. to 50° C., preferably 10° C. to 40° C., and particularly preferably at 25° C. The third step of the reaction (cyclization) may be carried out in a temperature range from 20° C. to 80° C., preferably 40° C. to 70° C., and particularly preferably at 55° C.

The typical course of the process is characterized by the following steps:

a) activation of the 2-propyl-4-methyl-1H-benzimidazole-6-carboxylic acid or the salt thereof by a 1,3,5-triazine and a tertiary amine;

b) coupling of the activated carboxylic acid with N-methyl-o-phenylenediamine or the salt thereof to form the corresponding amide; and c) cyclization, by heating, of the amide obtained, to form 1,7'-dimethyl-2'-propyl-2,5'-bi-1H-benzimidazole. Purification steps may be inserted between steps (b) and (c). 1,7'-Dimethyl-2'-propyl-2,5'-bi-1H-benzimidazole is purified by crystallization.

The preparation of 1,7'-dimethyl-2'-propyl-2,5'-bi-1H-benzimidazole using the method described gives yields of more than 30%, preferably more than 60%, and has the following technical advantages, above all:

a) it uses moderate temperatures, preferably below 60° C., b) it avoids the use of phosphorus oxide as a coupling reagent, and c) it avoids the use of methanesulfonic acid for the cyclization.

The present invention further relates to 1,7'-dimethyl-2'-propyl-2,5'-bi-1H-benzimidazole of formula (I) prepared by the method as described, which is suitable for the preparation of the pharmaceutically active substance telmisartan

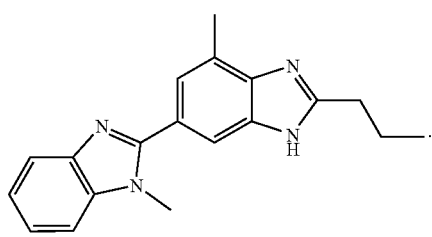

(I)

EXAMPLES

Example 1

Reaction in the Presence of 2-chloro-4,6-dimethoxy-1,3,5-triazine (Variant 1)

14.49 g of 2-chloro-4,6-dimethoxy-1,3,5-triazine is placed in 75 mL of methanol and cooled to about 0° C. with stirring. 9.07 mL of N-methylmorpholine is added dropwise over a period of 5 minutes at 0° C. and stirred for a further 40 minutes at 0° C.-5° C. 16.37 g of 2-propyl-4-methyl-1H-benzimidazole-6-carboxylic acid is added to the clear solution and this is rinsed with 30 mL of methanol at 0° C. After 2 hours at 0° C. and 2 hours at 10° C., 15 g of N-methyl-o-phenylenediamine phosphate salt is added and the mixture is rinsed with 7.5 mL of methanol and the suspension is stirred for another 30 minutes at 10° C. and then for 2 hours at reflux temperature. The mixture is then left to cool to ambient temperature (normal room temperature) overnight with slow stirring. The resulting crystal slurry is cooled to 5° C. and after 2 hours' slow stirring it is suction filtered. The crystals are washed with ice-cold methanol. Yield: 16.91 g (69.9% of theory); HPLC: 77.9%.

Example 2

Reaction in the Presence of 2-chloro-4,6-dimethoxy-1,3,5-triazine (Variant 2)

0.88 g of 2-chloro-4,6-dimethoxy-1,3,5-triazine in 20 mL of methanol are taken and cooled to about 0° C. with stirring. 0.55 mL of N-methylmorpholine is added dropwise at 0° C.-5° C. and the mixture is stirred for another 40 minutes at 0° C.-5° C. 1.09 g of 2-propyl-4-methyl-1H-benzimidazole-6-carboxylic acid is added to the clear solution and this is then rinsed with 10 mL of methanol at 0° C. After 1 hour at 0° C. and 1 hour at ambient temperature (normal room temperature), 1.0 g of N-methyl-o-phenylenediamine phosphate salt is added and the suspension is stirred overnight and then refluxed for 2 hours with stirring. The mixture is then left to cool to ambient temperature overnight with slow stirring. The crystals are suction filtered and washed with methanol. Yield: 0.55 g (34.2% of theory); HPLC: 97.7%.

Example 3

Reaction in the Presence of 2-chloro-4,6-dimethoxy-1,3,5-triazine (Variant 3)

0.97 g of 2-chloro-4,6-dimethoxy-1,3,5-triazine in 20 mL of 2-propanol are taken and cooled to about 0° C. with stirring. 0.6 mL of N-methylmorpholine is added dropwise at 0° C. and the mixture is stirred for another 40 minutes at 0° C.-5° C. 1.09 g of 2-propyl-4-methyl-1H-benzimidazole-6-carboxylic acid is added to the thick white suspension and it is rinsed with 10 mL of 2-propanol at 0° C. After 1 hour at 0° C., the mixture is allowed to come up to ambient temperature (normal room temperature) and stirred some more. After 2 hours, the reaction mixture is almost in solution. Then the mixture is heated to 55° C. and over a period of 75 minutes 1.0 g of N-methyl-o-phenylenediamine phosphate salt are added and the mixture is stirred for another 10 hours. The mixture is then set aside and left to stand overnight. The crystals are suction filtered and washed with 2-propanol. Yield: 0.57 g (35.4% of theory); HPLC: 96.8%.

We claim:

1. A process for preparing 1,7'-dimethyl-2'-propyl-2,5'-bi-1H-benzimidazole of formula (I)

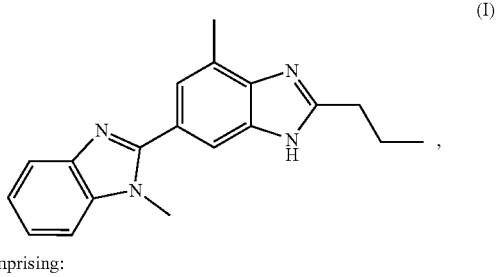

(I)

comprising:

reacting N-methyl-o-phenylenediamine of formula (II) or the salts thereof

(II)

with 2-propyl-4-methyl-1H-benzimidazole-6-carboxylic acid of formula (III) or the salts thereof

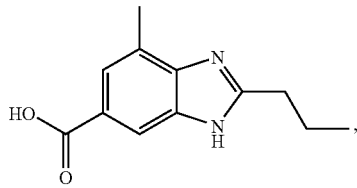
(III)

wherein the coupling and cyclization is achieved using 1,3,5-triazine and tertiary amine.

2. The process according to claim 1, wherein the coupling and cyclization is achieved using a 2-chloro-4,6-disubstituted-1,3,5-triazine.

3. The process according to claim 1, wherein the coupling and cyclization is achieved using 2,4,6-trichloro-1,3,5-triazine, 2-chloro-4,6-diphenoxy-1,3,5-triazine, 2-chloro-4,6-dibenzyloxy-1,3,5-triazine, 2-chloro-4,6-dimethoxy-1,3,5-triazine, 2,4-dichloro-6-phenoxy-1,3,5-triazine, 2,4-dichloro-6-benzyloxy-1,3,5-triazine, or 2,4-dichloro-6-methoxy-1,3,5-triazine.

4. The process according to claim 1, wherein a polar solvent is used.

5. The process according to claim 4, wherein the polar solvent is N,N-dimethylformamide, N,N-dimethylacetamide, dimethylsulfoxide, methanol, ethanol, or 2-propanol.

6. The process according to claim 1, wherein:
(a) the 2-propyl-4-methyl-1H-benzimidazole-6-carboxylic acid or the salt thereof is activated by a tertiary amine and a 1,3,5-triazine;
(b) the activated compound is coupled with N-methyl-o-phenylenediamine or the salt thereof to form an amide; and
(c) the amide obtained is cyclized by heating to form 1,7'-dimethyl-2'-propyl-2,5'-bi-1H-benzimidazole.

7. The process according to claim 6, wherein:
step (a) is carried out at a temperature of −10° C. to 25° C.;
step (b) is carried out at a temperature of 0° C. to 50° C.; and
step (c) is carried out at a temperature of 20° C. to 80° C.

8. The process according to claim 1, wherein a yield of more than 30% is achieved.

* * * * *